United States Patent [19]

Coker

[11] Patent Number: 5,363,841
[45] Date of Patent: Nov. 15, 1994

[54] RETRACTOR FOR SPINAL SURGERY

[76] Inventor: Wesley L. Coker, 601 Enquirer Ave., Nashville, Tenn. 37205

[21] Appl. No.: 86,941

[22] Filed: Jul. 2, 1993

[51] Int. Cl.$^5$ .............................................. A61B 17/02
[52] U.S. Cl. ..................................... 128/20; D24/135
[58] Field of Search .............................. 128/20, 17, 18; 606/191, 198; D24/135, 143

[56] References Cited

U.S. PATENT DOCUMENTS

| | | | |
|---|---|---|---|
| Re. 34,150 | 12/1992 | Santilli et al. | |
| 1,706,500 | 3/1929 | Smith | |
| 2,450,194 | 9/1948 | Glaser | |
| 2,642,862 | 6/1953 | Jackson | 128/20 |
| 4,048,987 | 9/1977 | Hurson | 128/20 |
| 4,156,424 | 5/1979 | Burgin | |
| 4,344,420 | 8/1982 | Forder | 128/20 |
| 4,421,107 | 12/1983 | Estes et al. | 128/20 |
| 4,726,356 | 2/1988 | Santilli et al. | |
| 4,747,394 | 5/1988 | Watanabe | |
| 4,747,395 | 5/1988 | Brief | 128/20 |
| 4,976,718 | 12/1990 | Daniell | D24/143 X |
| 4,989,587 | 2/1991 | Farley | |
| 5,052,373 | 10/1991 | Michelson | |
| 5,067,477 | 11/1991 | Santangelo | |
| 5,088,472 | 2/1992 | Fakhrai | |
| 5,167,223 | 12/1992 | Koros et al. | |

FOREIGN PATENT DOCUMENTS

| | | | |
|---|---|---|---|
| 3834358 | 4/1990 | Germany | 128/20 |
| 0908342 | 2/1982 | U.S.S.R. | 606/198 |
| 0963517 | 2/1983 | U.S.S.R. | 128/20 |
| 1292742 | 2/1987 | U.S.S.R. | 128/20 |
| 9216151 | 10/1992 | WIPO | 128/20 |

Primary Examiner—Richard J. Apley
Assistant Examiner—Donna L. Maraglio
Attorney, Agent, or Firm—I. C. Waddey, Jr.

[57] ABSTRACT

The retractor of the present invention has supporting arms connected at an angle to the retractor blades to remove the arms of the retractor from the top edges of the wound and thus allow for a greater amount of latitude in applying various mechanical devices to the spine. The angled arms on the retractor blades themselves placed these structures deep within the wound and thus apply distraction forces where they are needed the most—near the spine itself to spread the muscles away from the spine and make it easier to see.

The blades of this spinal retractor apply distraction forces deep within the wound where they are needed the most. On either side of the angled arms deep within the wound are vertical fingers projecting deeper into the wound on the lower portion and up out of the wound on the upper portion. The distances between the fingers provide further lateral angulation of instruments used in the wound itself for the placement of the spinal fixation devices.

This retractor also has a laterally projecting anchor peg extending from the muscle side of the retractor blade which is meant to lie beneath the dorsolumbar fascia. This anchor peg locks the retractor into the depths of the wound and prevents its migration up and out of the wound as is so frequently encountered in other types of spinal retractors.

16 Claims, 7 Drawing Sheets

RETRACTOR FOR SPINAL SURGERY

BACKGROUND OF THE INVENTION

The present invention relates generally to a surgical retractor and more specifically to a surgical spinal retractor designed to facilitate certain delicate surgical procedures. The present invention relates more specifically to a retractor that will better aid in the exposure of the thoracic and the lumbar spine during certain hardware insertion procedures.

It is now well recognized in the medical profession that back pain and pain in the extremities is often a direct result of pressure on the nerves of the spinal cord due to narrowing of the spinal column or misalignment of the vertebrae. The spine can be compressed by encroaching arthritic spurs, ruptured discs, enlarging soft tissue masses such as tumors, and pressure from infectious processes. In years past, these conditions of the spine were surgically corrected by bone decompression and soft tissue removal in association with a procedure called a fusion. Strips of grafted bone were placed adjacent to the vertebral segments causing them to grow together or "fuse". The resultant rigidity and realignment prevented further pressure on the nerves and stabilized the spinal column. In certain cases metal rods and hooks were attached to the bones to hold them in a specific position while they fused together.

In the past four to five years, these procedures have changed and there has been a dramatic increase in the use of spinal instrumentation devices in the treatment of this problem. Briefly, these devices involve the application of rather large screws, bolts, bars, and sometimes even rods in order to stabilize the spine. However, there has been an ongoing struggle to obtain adequate exposure of the bone structures surrounding the nerves making up the spinal column in order to insert the stabilizing devices. Because of the delicate nature of the surgery and the critical demand for visualization and placement of the stabilizing hardware, a need has developed for a retractor which allows better visual access to the spine and mechanical access to the bone structure where the hardware is being inserted.

In today's market, many different types of retractors are available which employ rack and pinion devices for the purpose of powering the retractor mechanism and holding the tissues apart. However, the retractor blades (the part of the distraction mechanism that actually enters into the wound and holds the muscle apart) currently available are a hinderance to visualizing the bones of the vertebral column and physical access to the bone by the necessary instrumentation. This deficiency in the prior art is what has led to the development of the retractor blades of the present invention.

Up to this point, the retractors that have been available for use in spinal surgery employ two arms which are perpendicular to a rack and pinion apparatus which is used to crank the arms apart. Extending at right angles from the arms down into the wound are various-sized retractor blades usually with one or more small teeth on the bottom of them. This particular design is flawed in two respects. The first flaw in these prior art devices is due to their inability to handle the tension inherent in the muscles and the fascial tissues in the back when the retractor is cranked open to spread the wound. As the two arms of the retractor are spread, a situation is created much like a bow string being drawn against the bow frame; the further the string is drawn (or the retractor arms are spread), the greater the pressure against the frame. And in the case of the surgical retractor, additional pressure is created because the retractor blades are extending into the wound. The further the blades extend into the wound, the greater the pressure. Because the blades are connected to the arms at one end and their other ends extend into the wound, there is a levering effect from the pressure of the muscles and fascial tissue on the teeth ends of the blades causing the blades to rotate about the pivot point created where they are connected to the arms of the retractor. The overall effect of these mechanics is that most retractors tend to work their way upward out of the wound because of the compressive forces of the muscles and fascial tissues.

The second problem with the prior art devices is that because the arms of the retractor lie along the skin at the top of the wound, they lie immediately in the way of the application of pedicle screw instrumentation apparatus. In the current procedure, screws are placed into the lateral or side portions of the spine into small, angled, structural parts of the vertebral body of the spinal column. It is absolutely critical that these screws be put in at a certain angle at each level. If the retractor has not been distracted far enough on either side of the wound, the large arms of the retractor block the appropriate angle being applied for the reaming and the application of these pedicle screws. The result of this can be disastrous in that the screw can be misapplied, and tilting either too far inward or outward can result in nerve damage or ineffective stabilization of the spine.

One obvious solution to the second flaw with the prior art devices is to simply crank the retractor open farther to spread the wound wider. However, spreading the wound wider tends to create tears in the muscles and flesh and impede the healing process as well as creating more pressure on the blades of the retractor, thus causing them to be more prone to work their way upwardly and out of the wound.

It will thus be appreciated by those skilled in the art that there is a need to provide a retractor which can accommodate the requirements of this new procedure without having to spread the wound wider. The desired device would spread the wound to make the spine visually and mechanically accessible without creating excessive tearing of the muscles and fascial tissue and without creating excessive pressure on the blades of the retractor to cause them to work their way up and out of the wound. This device is presently lacking in the prior art.

SUMMARY OF THE INVENTION

The retractor of the present invention is unique in that the angles of the supporting arms of the blades remove the arms of the retractor from the top edges of the wound and thus allow for a greater amount of latitude in applying various mechanical devices to the spine in varying angles so as to accurately place them within the bony channels previously described. Secondly, the angled arms on the retractor blades themselves placed these strong structures deep within the wound and thus apply distraction forces where they are needed the most-near the spine itself to spread the muscles away from the spine and make it easier to see.

In addition to the angled arms of the retractor, the blades themselves are unique. All other blades that I have seen illustrated and described drop perpendicularly from the retractor arms directly down into the wound and not only obstruct instrument placement but also apply distraction forces maximally on the skin and the upper edges of the wound. The blades of this spinal retractor apply distraction forces deep within the wound where they are needed the most. The two additional parts of this retractor which make it a substantial improvement over the prior art devices are that on either side of the angled arms deep within the wound are vertical fingers projecting deeper into the wound on the lower portion and up out of the wound on the upper portion. These fingers serve very much like an open hand in further grasping the muscle tissues and locking them out of the way. In addition to that, the distances between the fingers provide further lateral angulation of instruments used in the wound itself for the placement of the spinal fixation devices. This advantage is not present in any other spinal retractor and consequently instrument angles are severely compromised.

The third distinction of this retractor over the prior art is a laterally projecting anchor peg extending from the muscle side of the retractor blade which is meant to lie beneath the dorsolumbar fascia. This anchor peg further locks the retractor into the depths of the wound and prevents its migration up and out of the wound as is so frequently encountered in other types of spinal retractors.

The blades are supplied in various sizes and shapes in order to accommodate different wound depths. One variety is hinged in order to increase variation of blade depths. And while the detailed description of the preferred embodiment describes specific examples of the retractor, it will be appreciated that other embodiments of the invention may be designed within the scope of the claims.

DESCRIPTION OF THE PREFERRED EMBODIMENT

Figure 1:
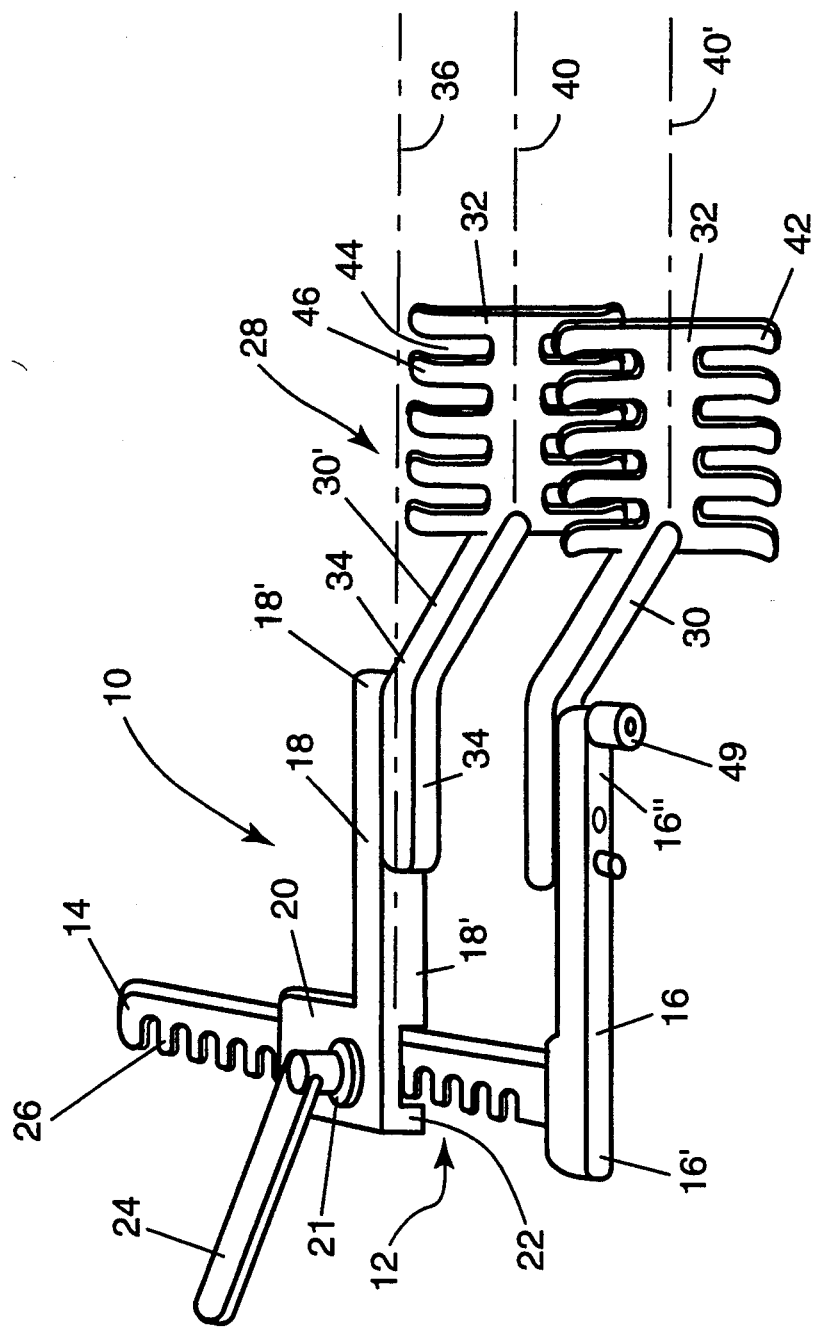
FIG. 1 is a perspective view of the retractor of the present invention.

Referring now to the drawings, where like reference numerals represent like elements in the invention, the following detailed description of the preferred embodiment of my invention will be understood by those of ordinary skill in the art.

Referring first to FIG. 1, a retractor 10 is shown generally in perspective view. The retractor 10 includes a rack and pinion assembly 12 which includes a bar 14, a first arm 16 and a second arm 18. Each arm has a proximal end 16',18' and a distal end 16", 18". The proximal end 16' of arm 16 is fixedly attached to one end of the bar 14.

The rack and pinion assembly 12 includes a pinion housing 20 which has a channel 22 passing through it. The bar 14 passes through the channel 22 and is slidably engaged within the pinion housing 20. The pinion housing 20 fits about the bar 14 to hold the housing 20 in a fixed relationship to the bar 14 as the housing moves laterally along the bar 14. The proximal end 18' of arm 18 is fixedly connected to the pinion housing 20 so that as the housing moves along the bar 14, the arm 18 likewise moves to and from in relationship to the arm 16.

Rotatably mounted within the housing 20 is a pivot shaft 21 to which is attached a set of pivot pins (not shown). As the pivot shaft 21 is rotated by the crank 24, the pins alternatively engage the gear 26 to cause the pivot housing to move in one direction along the bar 14 when the crank is rotated clockwise and in the opposite direction along bar 14 when the crank is rotated counterclockwise.

The rack and pinion assembly described to this point is off-the-shelf hardware readily available from manufacturers of medical devices and peripherals. The rack and pinion assembly used in my invention is a Valin Hemilaminectomy Retractor sold by V. Mueller Company which is a division of Baxter Healthcare Corporation. Another such device is the Buford Finochietti Rib Retractor distributed by Codman & Schurtleff, Inc., a division of Johnson & Johnson, Inc. Likewise, rack and pinion systems of this type are described in the patent literature. For example, see the Rack & Pinion System illustrated in U.S. Pat. No. 5,167,223 to Koros et al.

In addition to the rack and pinion system for use with the retractor of the present invention, one could use other types of mechanical structures to effect the spreading of the two arms of the retractor. For example, earlier devices used a ratchet system. Examples of such earlier prior art devices are shown in U.S. Pat. No. 2,450,194 to Glasser and U.S. Pat. No. 1,706,500 to Smith.

From the foregoing brief description of the prior art, it will be readily understood that a number of retractors have been available on the marketplace for spreading the wound created by an incision in a patient's body prior to conducting the surgical procedure. The present invention is particularly concerned with spreading the wound when an incision is made to perform back surgery, but the teachings of this invention may be applicable to other types of surgery. However, the present invention is particularly adaptable to back surgery because of the strength of the back muscles and facial tissue which requires a retractor of substantial strength and stability.

Figure 2:
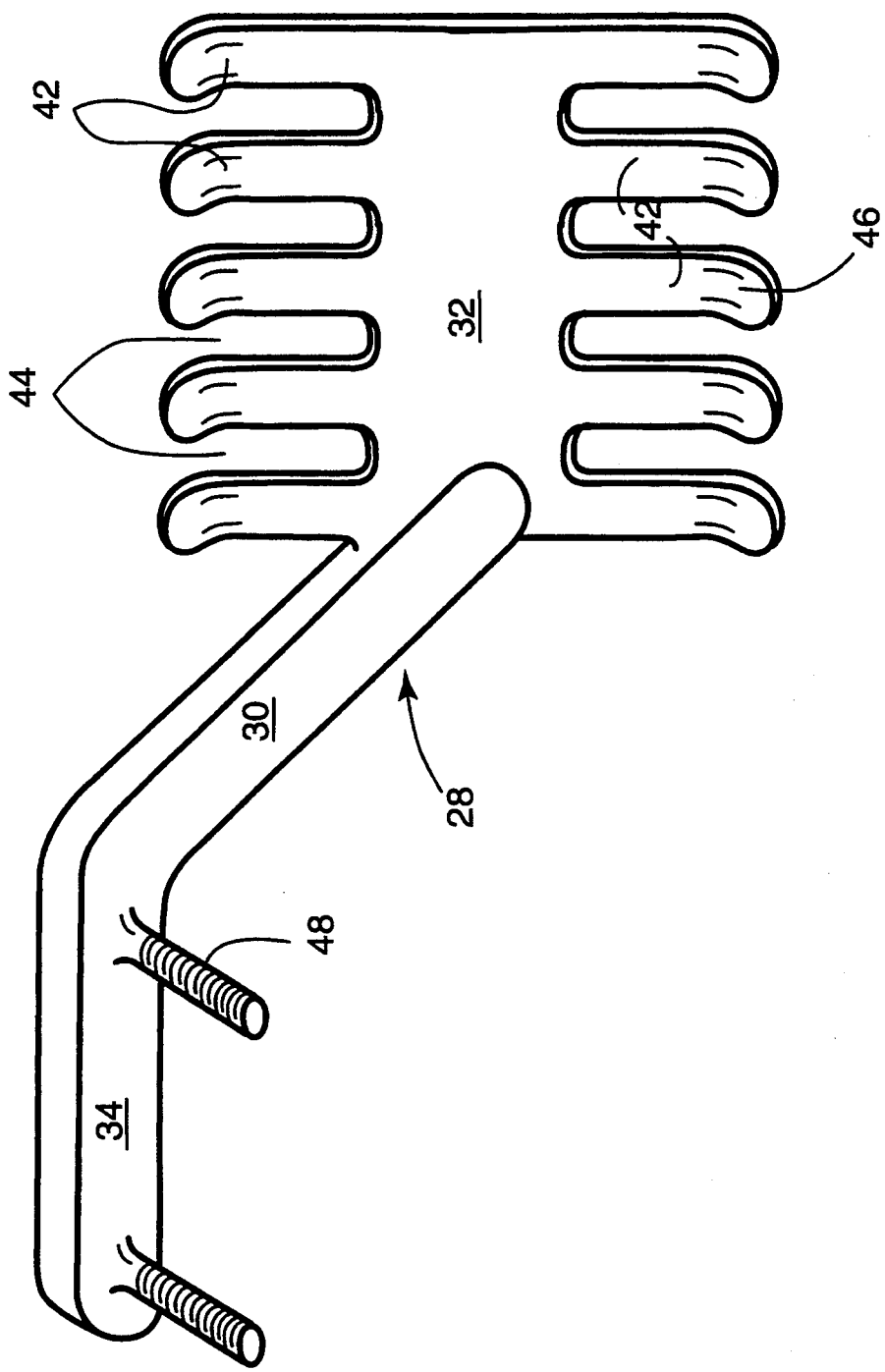
FIG. 2 is a perspective view of one of the retractor blades of the present invention.

Referring now to FIG. 2, a perspective illustration of one embodiment of the retractor blades of the present invention can be seen. The retractor blades include an angle arm 30. As can be seen in FIG. 1, two retractor blades of the present invention are mounted on the distal ends 16" and 18" of the two arms 16 and 18, and the angle arm of the second retractor blade is marked 30'. For the purpose of the description of this invention, only one of the retractor blades will be described, but it will be appreciated that the blades are mirror images of each other and the description of the operation of the present invention will give a more specific description of the operation of the two retractor blades in cooperation.

Referring back to FIG. 2, it can be seen that a retractor plate 32 is attached to one end of the angle arm 30. At the other end of the angle arm 30 is the attachment section 34. Because the angle arm 30 connects the attachment section 34 to the retractor plate 32, the retractor plate is offset from the arms 16 and 18 of the retractor. To illustrate this offset, an axis line 36 for the arm 18 is illustrated in FIG. 1. There is also an axis line 40 for the retractor plate 32. The effect of this offset is that the retractor plate 32 drops below the level of the arm 18 due to the angle arm 30 of the retractor blades 28. Thus, the retractor plate 32 is positioned within the cavity created by the surgical incision and can be placed against the face of the wound to spread the cavity when the crank 24 is turned on the rack and pinion device.

Before getting to the operation of the retractor of the present invention however, additional detail is necessary to describe the preferred embodiment of the retractor plates. As can be seen from FIGS. 1 and 2, the retractor plate has fingers 42 which are separated by gaps 44. The fingers have tips 46 which, with respect to each retractor plate are curved away from the point of incision and into the flesh of the patient.

The retractor blades also have studs 48 projecting perpendicularly from the attachment section 34 to pass through holes (not shown) in the ends of the arms 16 and 18. The studs 48 may be threaded and they are secured onto the arms 16 and 18 by nuts 49 which threadably engage the studs 48 and tighten the attachment section of the retractor blades onto the arms 16 and 18 of the retractor.

Figure 2A:
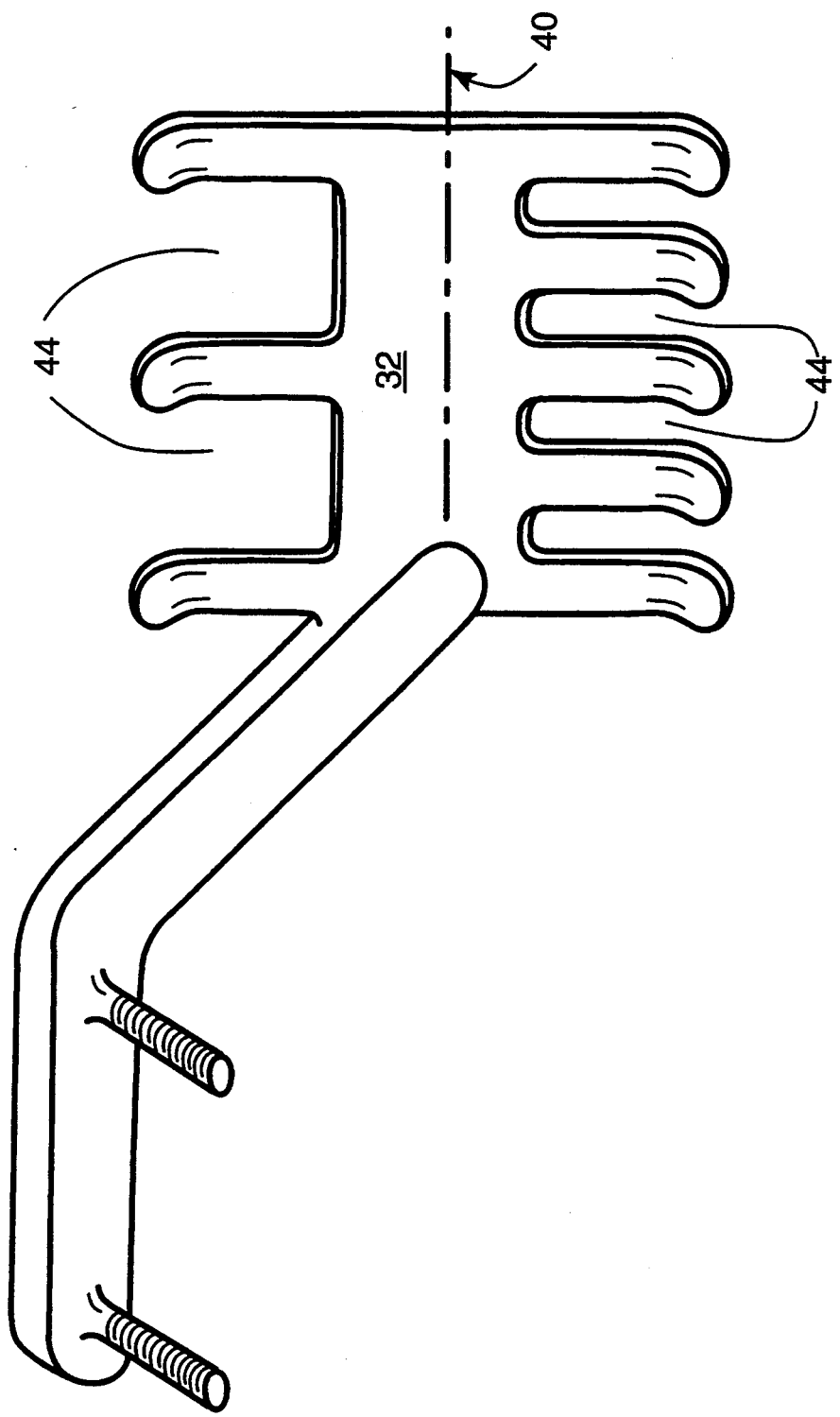
FIG. 2a is a perspective view of an alternative construction of a retractor blade of the present invention.

Referring to FIG. 2a, a modified version of the retractor blades is shown. In FIG. 2a, the gaps 44 on the portion of the retractor plate above the axis 40 are substantially wider than the gaps 44 below the axis. In each instance, the retractor plates 32 have fingers that extend in opposite direction from the axis 40 of the retractor plate so that in operation, the top fingers extend upwardly, projecting towards the patient's skin and the lower fingers extend downwardly, projecting towards the patient's spine. The gaps 44 projecting towards the patient's skin are much wider than the gaps 44 projecting towards the patient's spine. This will allow greater flexibility in the use of instrumentation involved in the surgical procedure during the performance of which this retractor is designed to be used.

Figure 3:
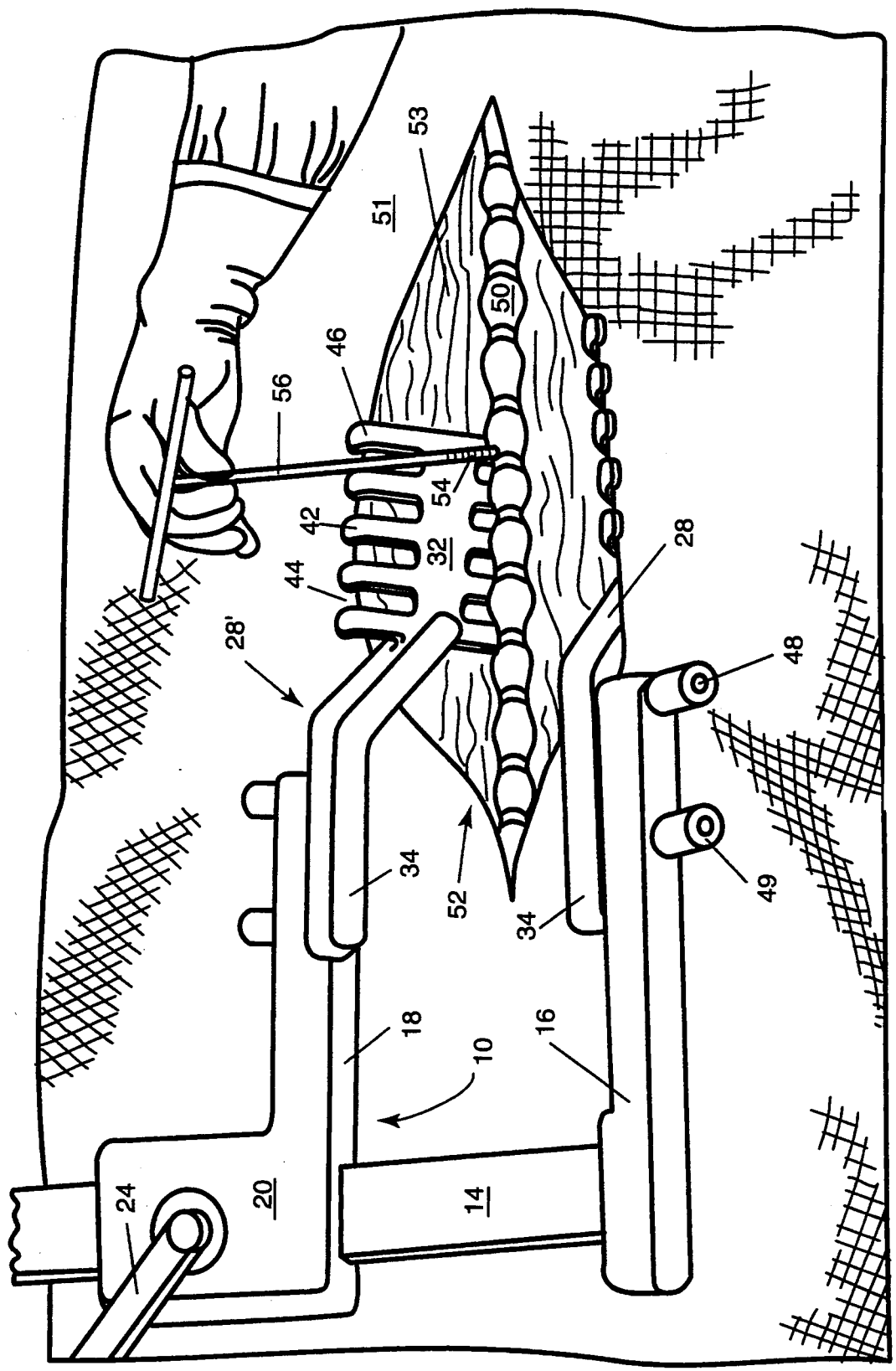
FIG. 3 is a perspective view of a retractor of the present invention in use.

Referring now to FIG. 3, the retractor of the present invention in use is illustrated. As can be seen from FIG. 3, the retractor 10 is laid flat on the patient's back and for the purpose of this description, it will be assumed that this patient is lying on his/her stomach and that the patient's back is in a horizontal plane. More generally, the description of the operation and use of this invention refers to horizontal and vertical relationships, top and bottom relationships and up and down relationships based on the assumption that the patient's back is in a horizontal plane and that the retractor of the present invention is lying flat on the patient's back. Obviously, if the patient is reoriented, the relative relationships will remain the same but descriptions of horizontal and vertical, up and down, top and bottom would be reoriented based on the reorientation of the patient.

The bar 14 is shown in FIG. 3 without the gear 26 since the rack and pinion assembly is only shown in schematic form without the details illustrated in FIG. 1. Obviously, in operation, the rack and pinion assembly would be as previously indicated. The bar 14 lies flat on the patient's back and the arms 16 and 18 extend perpendicularly from the bar 14 and also lie flat on the patient's back. Thus, the bar 14 and the arms 16 and 18 are in the same horizontal plane.

As indicated above, the pinion housing 20 fits about the bar 14 to traverse the bar 14 in slidable engagement therewith. As the crank 24 is rotated in one direction, the arm 18 will move toward the arm 16 and as the crank 24 is rotated in the opposite direction, the arm 18 will move away from the arm 16.

Two of the retractor blades 28 are attached to the retractor, one being attached to arm 16 and the other being attached to the arm 18. The retractor blades are attached at their attachment section 34 when the studs 48 pass through the openings (not shown) in the arms 16 and 18. Nuts 49 are screwed onto the threaded studs 48 to tighten the attachment section 34 of the retractor blades 28 to the arms 16 and 18.

It is possible, of course, to have the retractor blades 28 integrally formed with the arms 16 and 18 of the retractor. However, such a construction would make the device much more expensive because if one needed a different size retractor plate, or a different depth of penetration of the retractor blade into the wound, it would be necessary to have a different size and shape retractor assembly altogether. By the construction of the present invention with the retractor blades 28 being detachably connected to the arms 16 and 18, various sizes and shapes of retractor blades may be used, depending upon the size of the patient, the depth of the incision and the like.

During the procedure for which this retractor is particularly adapted, an incision 52 is made in the patient's back. After cutting the skin 51, the incision passes through the back muscles and fascia tissues 53 (reference can also be had to FIG. 7 and 8 to more clearly visualize this aspect of the procedure). The retractor (with the retractor blades 28 in a collapsed position with arms 16 and 18 being as close to each other as possible) is then inserted into the wound so that the retractor blades project down into the wound and the upwardly projecting fingers 42 extend just to the skin of the patient or just below the skin of the patient. The crank 24 is then turned in the direction to spread the arm 18 from the arm 16 thereby causing the retractor blade 28' to move away from the retractor blade 28 and spread the wound. The spreading of the wound exposes the spine 50 so that the surgical procedure contemplated herein can be performed.

The retractor plates 32 extend downwardly into the wound and their axis 40 will be substantially below the point of incision 52 and the skin 51 of the patient. The fingers 42 that project upwardly will, in most cases, have their fingertips 46 projecting away from the point of incision and be at a level below the bottom-most portions of the arms 16 and 18. The fingers 42 that project downwardly from the retractor plates 32 are placed to either side of the spine and are designed to pull the muscles and fascia tissue away from the spine to expose the spine for the operative procedure as is herein contemplated.

The hardware used in this procedure, called a spinal fixation device 54 consists of threaded screws placed within the spinal bones and these are then interconnected with plates or rods by means of locking nuts. The holes for the fixation screws must be drilled and tapped by devices connected to rods with handles. The rod 56 passes through the gap 44 between the fingers 42 projecting upwardly from the axis of the retractor plate 32. By virtue of the gaps 44 between the fingers 42, the rod 56 can be placed at a greater angle to the vertical than would otherwise be the case if the retractor plates were of the type as shown in the prior art in FIGS. 4a, 4b and 4c. Also, as can be seen in FIGS. 2a, the retractor plate can be made with wider gaps 44 to allow greater lateral movement of the rod to get better angular direction on the rod (and thereby the spinal fixation device) in order the properly place the spinal fixation device in the patient. As will be apparent from FIG. 3, the surgeon will manipulate the end of the rod 56 opposite the point where the rod connects to the spinal fixation device in order to make the proper connection of the spinal fixation device with the spine 50.

Figure 4:
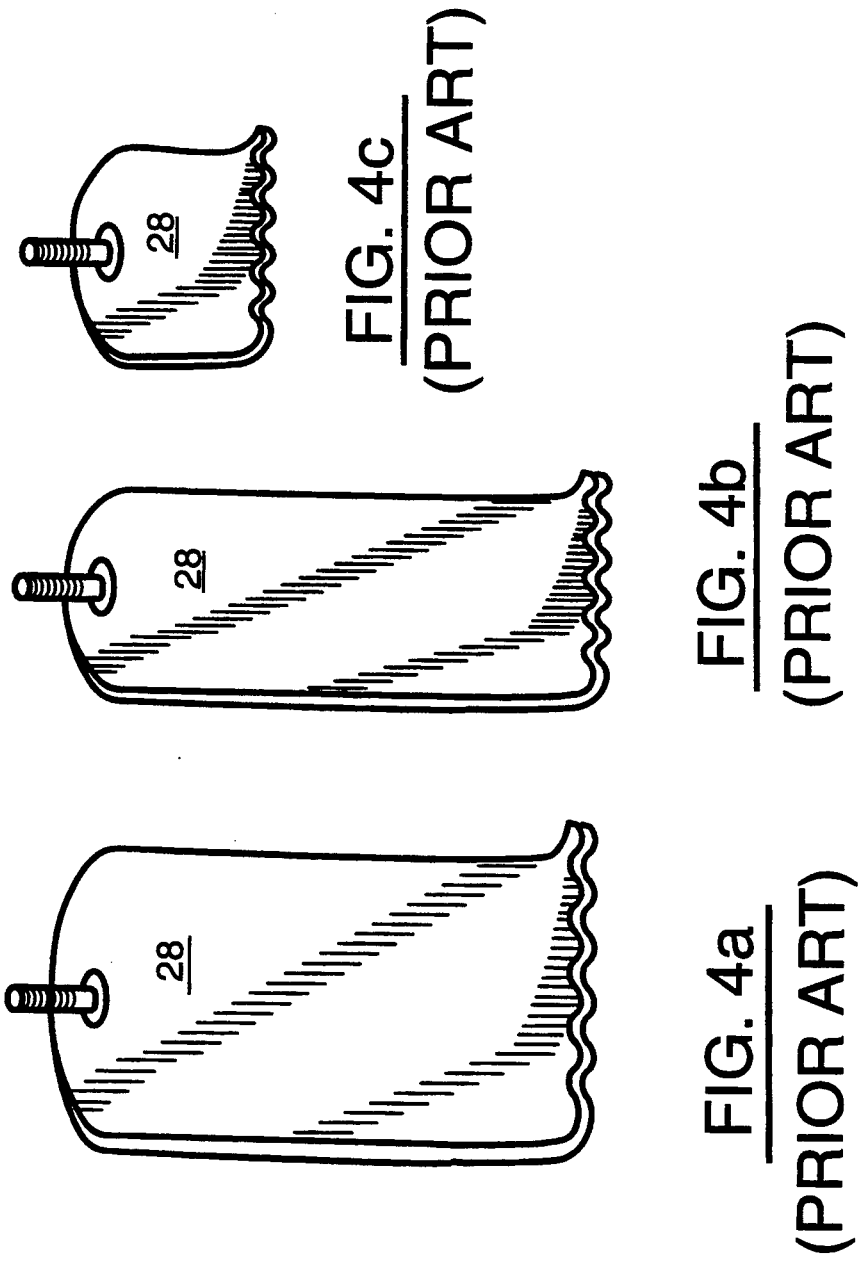
FIGS. 4a, 4b and 4c illustrate retractor plates of the prior art.
Figure 7:
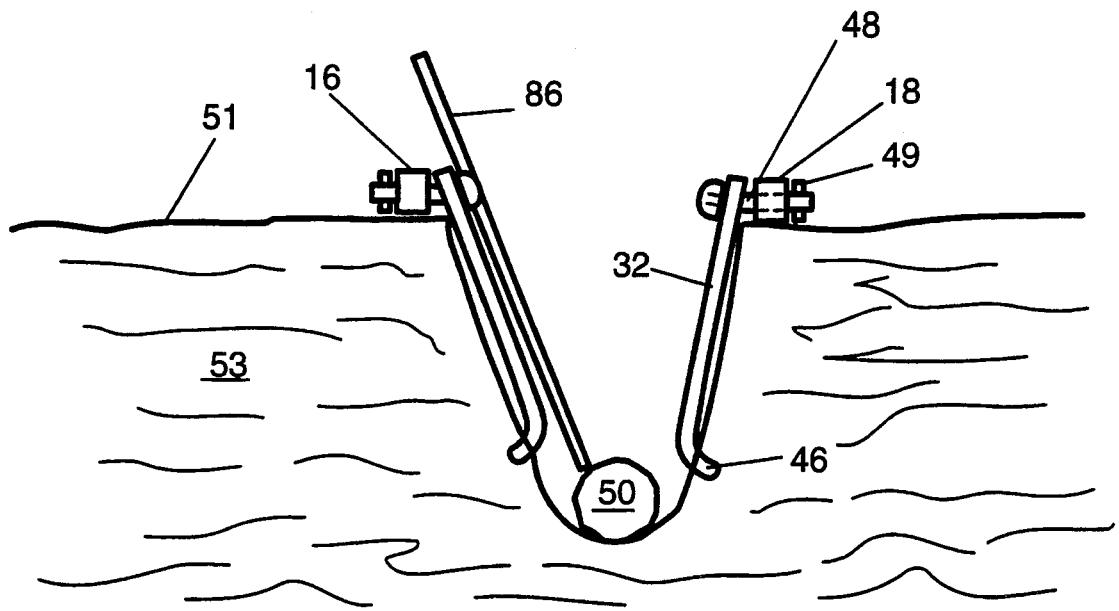
FIG. 7 is an illustration of a cross section of a surgical opening showing the retractor blades of the prior art in use.
Figure 8:
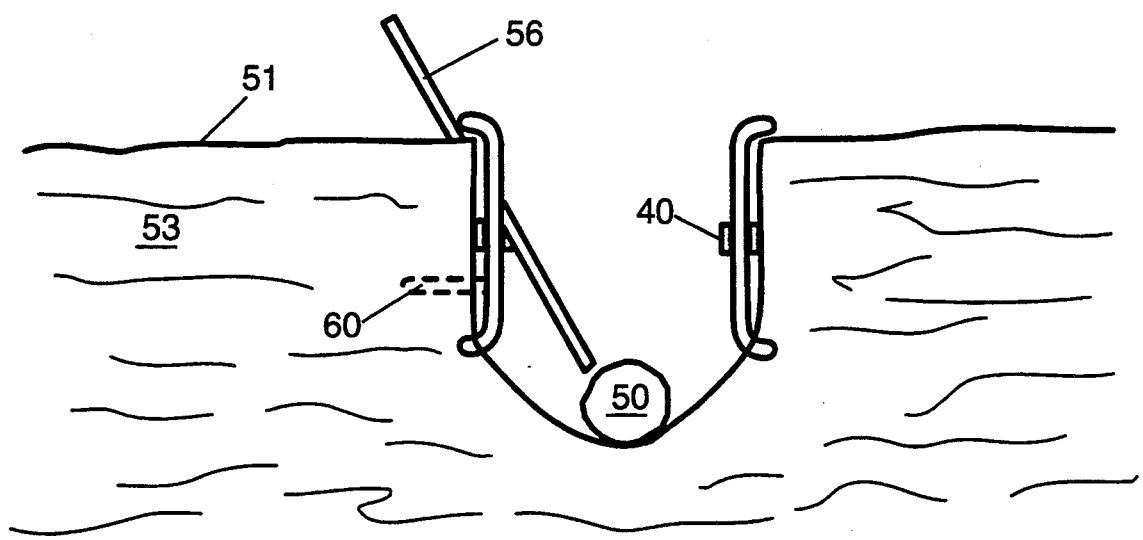
FIG. 8 is a cross section of a surgical opening showing the retractor of the present invention in operation.

Referring now to FIGS. 7 and 8, the distinctions between the present invention and the prior art devices are illustrated. The prior art retractor plates as shown in FIG. 4a, 4b and 4c would be connected to the arms 16 and 18 by any convenient bolt or stud structure 48, 49. The plate 32 of the prior art is connected at one end to the arms 16, 18 and depends down into the open wound with the opposite end of the retractor plate 32 having outwardly curved tips 46 to grab the flesh and attempt to spread it away from the spine 50. However, as can be seen in the illustration of FIG. 7, because of the extreme pressures that the retractor assembly faces, there will be a levering effect on the retractor blades causing them to pivot about the point 48 at which they are connected to the arms 16 and 18. This causes the retractor plates 32 to be at an angle to the vertical. For this reason, the retractor plates 32 do not spread the wound as well as the device of the present invention and there is less visual and physical access to the spine because the wound is not spread as a result of the tendency of the blades to rotate angularly against a pivot point 48.

It will also be seen from FIG. 7 that the rod 56 can only be angled so far as it can move into contact with either the top of the plate 32 or, if it is moved away from plate 32, only so far as the arms 16, 18 would allow. Finally, in reference to the prior art device as is illustrated in FIG. 7, because the retractor plates 32 tend to be angled against the wound rather than perpendicular to the wound, there is a tendency of the retractor to ride upwardly out of the wound in response to the pressures exerted upon it. The retractor has a tendency to "squirt" out of the wound; although this reaction is a gradual effect of the pressure of the muscle and fascia tissue of the patient and tends to occur gradually rather than in an instantaneous manner. However, the tendency of the retractor to ride upwardly, is a significant detraction of the prior art devices.

Comparing the prior device in use as shown in FIG. 7 to the device of the present invention as shown in FIG. 8, it can be seen that because the pressures of the arms 16 and 18 in spreading the wound are translated to the level of the axis 40 of the retractor plates, the retractor plates tend to remain vertical rather than becoming angled to the vertical. The retractor plate gets pressure at the point of incision and it likewise receives pressure at the tips of the fingers protruding downwardly into the wound. However, the point of force of the retractor is placed substantially down into the wound so as to decrease the leveraging effect onto the retractor blades.

In use, the retractor plates of the present invention, as is illustrated in FIG. 8, cause the wound to be spread wider at the critical area around the spine; thus giving greater visual and physical access to the spine 50.

Referring again to FIG. 8, the physical access to the spine 50 is enhanced because the fingers 42 extending upwardly from the axis 40 have gaps 44 in them through which the rod 56 can pass. This allows the rod to be deployed at a greater angle to the vertical than is possible with the prior art devices because the rod, when used in connection with the prior art devices would either hit the retractor plate 32 or one of the arms 16, 18. In the present invention, the arms 16 and 18 are removed from the portion of the wound where the operative procedures are being performed and the first pediment to the rod would be at the bottom of the gaps 44 between the fingers 42. As indicated, this allows the rod 56 to be placed at a greater angle to the vertical than is possible with the prior art devices and is a significant advantage when performing the procedures involved in this operation.

Figure 5:
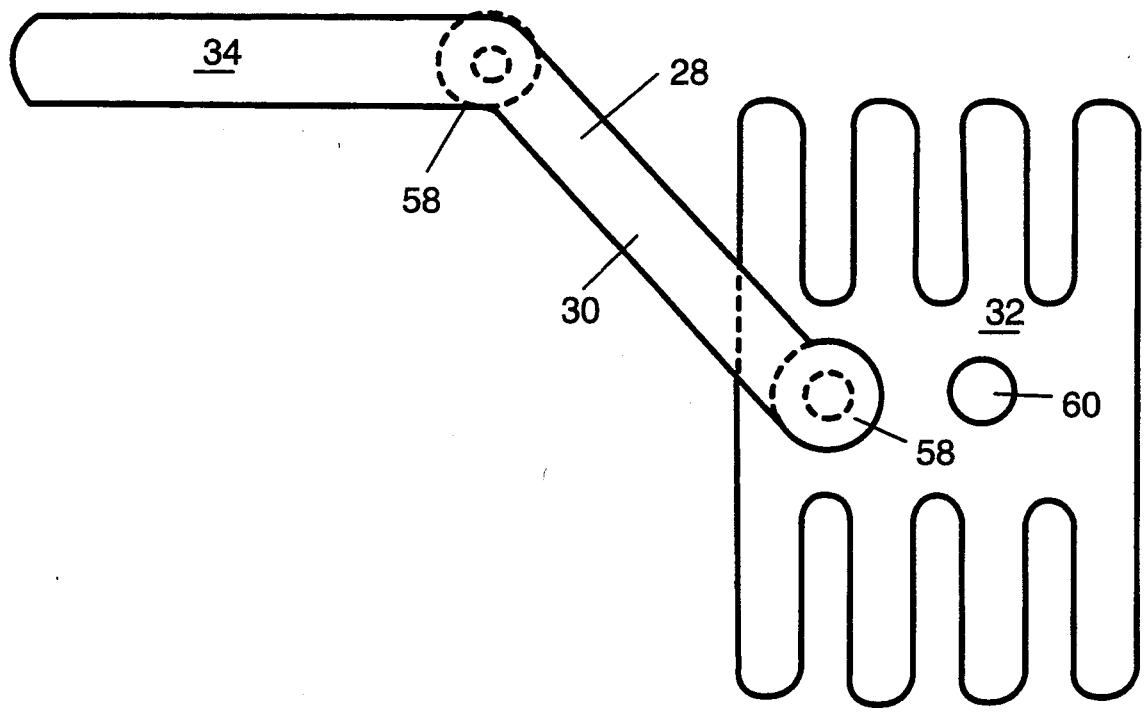
FIG. 5 is a plain view of the retractor blade of the present invention with hinged angle arms and an anchor peg.

Referring back to FIGS. 5 and 6, additional features of the present invention are illustrated. FIG. 5 shows a retractor blade 28 that has a pivotal connection 58 between the angle arm 30 and the attachment section 34 as well as between the angle arm 30 and the plate 32. Thus, the pivotal connection can be adjusted to increase or decrease the angle between the angle arm 28 and the attachment section 34 and likewise to increase or decrease the angle between the angle arm 38 and the axis 40 of the retractor plate 32. Once the proper angle has been established, the pivotal connections can be tightened down to fixedly secure the relative parts in their adjusted position. This will allow one to use the same retractor blades for different procedures by raising or lowering the retractor plates within the depths of the wound.

Figure 6:
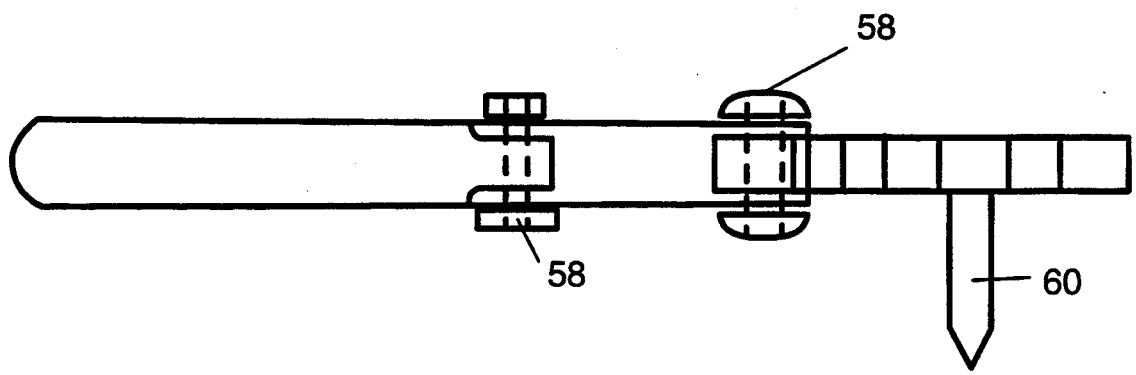
FIG. 6 is a top view of the retractor blade shown in FIG. 5.

Also illustrated in FIGS. 5 and 6 is a anchor peg 60 which extends perpendicularly from the face of the plate 32. The anchor peg 60 can also be seen in FIG. 8 as it projects into the wall of the wound created by the surgical incision and into the muscle and fascia tissue of the patient. This anchor peg 60 will keep the retractor plates from riding upwardly out of the wound as is the tendency of the prior art devices. Clearly, an anchor peg can be made a part of both retractor blades 28 and 28' in order to keep both sides of the retractor anchored within the wound so that this procedure can be performed.

Although there have been described particular embodiments of the present invention of a new and useful Retractor for Spinal Surgery, it is not intended that such references be construed as limitations upon the scope of this invention except as set forth in the following claims.

What I claim is:

1. A surgical retractor including:
   a. a pair of arms defining a first plane,
   b. means for maintaining said arms within said first plane and substantially parallel to each other,
   c. means for moving one of said arms relative to the other of said arms and for holding said one arm apart from said other arm against collapsing pressure,
   d. each of said arms having a proximal end and a distal end,
   e. a pair of retractor blades,
   f. each of said retractor blades having a connector section, an angle arm and a retractor plate, g. one of said retractor blades being connected at said connector section to the distal end of one of the arms and the other of said retractor blades connected to the distal end of the other of said arms, said connector sections being substantially coplanar with said first plane, said angle arms being fixedly attached to said connector section, and said retractor plate extending in a plane substantially transverse to said first plane; and h. wherein said angle arms cause said retractor plates to be off-set from said connector sections whereby said retractor plates extend beyond the distal end of the arm to which the said retractor blade is attached and down into a wound created by an incision when the retractor is employed in a surgical procedure.

2. A surgical retractor as claimed in claim 1 wherein said retractor plate has an axis passing substantially through the point of connection between the angle arm and the retractor plate, said axis being substantially parallel to the connector section, and wherein said retractor plate has sets of fingers projecting outwardly from the axis of the plate, one of the said sets of fingers projecting generally in the direction of the connector section and another of the said sets of fingers projecting substantially in the opposite direction.

3. A surgical retractor as claimed in claim 2 wherein there are gaps between the fingers.

4. A surgical retractor as claimed in claim 3 wherein the gaps between the fingers of the set of fingers projecting generally toward the connector section are larger than the gaps between the fingers of the set of fingers projecting away from the connector section.

5. A surgical retractor as claimed in claim 1 further including an anchor peg connected to the retractor plate and extending substantially perpendicularly therefrom.

6. A surgical retractor as claimed in claim 5 wherein the direction of projection of the anchor peg is away from the other arm of the retractor.

7. A surgical retractor including:
a. a first arm and a second arm, each of said arms having a proximal end and a distal end;
b. said first arm and said second arm each lying substantially in the same plane;
c. a cross bar;
d. the proximal end of the first arm connected to the cross bar;
e. means slidably connecting the proximal end of the second arm to the cross bar;
f. means enabling the second arm to traverse the cross bar, thereby being movable selectively toward and away from the first arm;
g. said means further enabling the second arm to be fixed in selected spacial relationship to said first arm;

h. a first retractor blade connected to the distal end of the said first arm;
i. a second retractor blade attached to the distal end of the second arm;
j. said retractor blades each having a connector section, an angle arm and a retractor plate;
k. the connector sections of the first and second retractor blades being connected to the distal ends of the first and second arms, respectively
l. each retractor plate having an axis of symmetry, said axis lying in a plane substantially parallel to the plane in which the first and second arms lie; and
m. said retractor plates being spaced beyond the distal ends of the arms and below the plane in which the first and the second arms lie.

8. The surgical retractor claim 7, wherein the retractor plate has fingers with gaps between the fingers.

9. The surgical retractor claimed 8 in claim 8 wherein there are two sets of the fingers, one set projecting upwardly and another set projecting downwardly.

10. The surgical retractor claimed in claim 7 including an anchor peg projecting substantially perpendicularly from at least one of said retractor plates.

11. A surgical retractor blade kit including a pair of retractor blades designed for use with a surgical retractor wherein said surgical retractor includes means for spreading a pair of arms and for holding the arms in a fixed relationship, the retractor blades of said retractor blade kit being designed for attachment to the end of each arm; each retractor blade of said retractor blade kit including a retractor plate and means off-setting the location of the retractor plate from the point of attachment between the retractor blade and the arm so that the retractor plate extends beyond the end of the retractor arm and, when the retractor arm is held in a horizontal position, below the retractor arm, the off-setting means including an angle arm having an axis along the length thereof, and said retractor plate having an axis along the length thereof, the axis of the angle arm and the axis of the retractor blade lying in substantially the same plane and at an angle to each other.

12. The retractor blade kit claimed in claim 11, wherein each retractor plate has fingers with gaps between the fingers.

13. The retractor blade kit claimed in claim 12 wherein there are two sets of the fingers, one set projecting upwardly and another set projecting downwardly.

14. The retractor blade kit claimed in claim 13 wherein there are fewer fingers projecting upwardly than downwardly.

15. The retractor blade kit claimed in claim 11 including an anchor peg projecting substantially perpendicularly from each retractor plate.

16. The retractor blade kit claimed in claim 11 including means for adjusting the plate relative to a remainder of the blade so that the depth of the plate relative to the retractor can be varied.

* * * * *